(12) United States Patent
Weeber et al.

(10) Patent No.: US 9,097,636 B2
(45) Date of Patent: Aug. 4, 2015

(54) THERMOELECTRIC COMPONENT WITH PLASMONIC GUIDE, INTEGRATING A DEVICE FOR MEASURING THE POWER COUPLED IN THE GUIDED MODE

(75) Inventors: Jean-Claude Weeber, Dijon (FR); Alain Dereux, Varois Et Chaignot (FR)

(73) Assignees: CENTRE NATIONAL DE LA RECHERCHE SCIENTIFIQUE, Paris (FR); UNIVERSITE DE BOURGOGNE, Dijon (FR)

( * ) Notice: Subject to any disclaimer, the term of this patent is extended or adjusted under 35 U.S.C. 154(b) by 713 days.

(21) Appl. No.: 13/475,462

(22) Filed: May 18, 2012

(65) Prior Publication Data

US 2013/0128917 A1    May 23, 2013

(30) Foreign Application Priority Data

May 19, 2011    (FR) ..................................... 11 54393

(51) Int. Cl.

| G01K 7/04 | (2006.01) |
|---|---|
| G01N 25/00 | (2006.01) |
| B82Y 20/00 | (2011.01) |
| G01K 7/08 | (2006.01) |
| G02B 6/122 | (2006.01) |
| G01N 21/552 | (2014.01) |
| G01N 27/00 | (2006.01) |
| G01K 7/02 | (2006.01) |

(52) U.S. Cl.
CPC ................ *G01N 25/00* (2013.01); *B82Y 20/00* (2013.01); *G01K 7/08* (2013.01); *G02B 6/1226* (2013.01); *G01K 7/02* (2013.01); *G01K 7/04* (2013.01); *G01N 21/553* (2013.01); *G01N 27/002* (2013.01)

(58) Field of Classification Search
CPC ..... G01N 27/002; G01N 21/553; G01K 7/02; G01K 7/04; G02B 6/1226
USPC ................................ 374/45, E7.004, E7.009
See application file for complete search history.

(56) References Cited

U.S. PATENT DOCUMENTS

| 5,792,667 | A | 8/1998 | Florin et al. |
|---|---|---|---|
| 7,043,134 | B2 * | 5/2006 | Berini et al. .................. 385/147 |
| 8,279,444 | B2 * | 10/2012 | Boukherroub et al. ....... 356/445 |
| 2003/0223668 | A1 | 12/2003 | Breukelaar et al. |
| 2005/0058425 | A1 * | 3/2005 | Berini et al. .................. 385/147 |
| 2012/0019907 | A1 * | 1/2012 | Argoul et al. ................. 359/371 |

OTHER PUBLICATIONS

Sergey I. Bozhevolnyi, et al., "Integrated Power Monitor for Long-Range Surface Plasmon Polaritons", Optics Communications, Nov. 2005, pp. 51-56, vol. 255, XP002669882.
Heeres, R. W. et al., "On-Chip Single Plasmon Detection," Nanoletters, pp. 661-664 (2010).

(Continued)

*Primary Examiner* — Lisa Caputo
*Assistant Examiner* — Jonathan Dunlap
(74) *Attorney, Agent, or Firm* — Baker & Hostetler LLP

(57) ABSTRACT

A thermoelectric component comprises integrated into the component: a plasmonic waveguide, an exciter element for the guided plasmonic mode, a device for measuring the power dissipated during propagation along the plasmonic waveguide, characterized in that the measurement device comprises, associated with the plasmonic guide, a thermocouple junction with two electrodes, one of the electrodes including the plasmonic waveguide.

21 Claims, 15 Drawing Sheets

(56) References Cited

OTHER PUBLICATIONS

Innes, R. A. and Sambles, J. R., "Simple Thermal Detection of Surface Plasmon-Polaritons," Solid State Communications, vol. 56, No. 6, pp. 493-496 (1985).

Ditlbacher, F. R. et al., "Organic Diodes as Monolithically Integrated Surface Plasmon Polariton Detectors," Applied Physics Letters, 89, 161101, pp. 1-3 (2006).

Akbari, A. and Berini, P., "Schottky Contact Surface-plasmon Detector Integrated with an Asymmetric Metal Stripe Waveguide," Applied Physics Letters, 95, 021104, pp. 1-3 (2009).

Falk, A. L. et al., "Near-field Electrical Detection of Optical Plasmons and Single-plasmon Sources," Nature Physics, vol. 5, pp. 475-479 (2009).

* cited by examiner

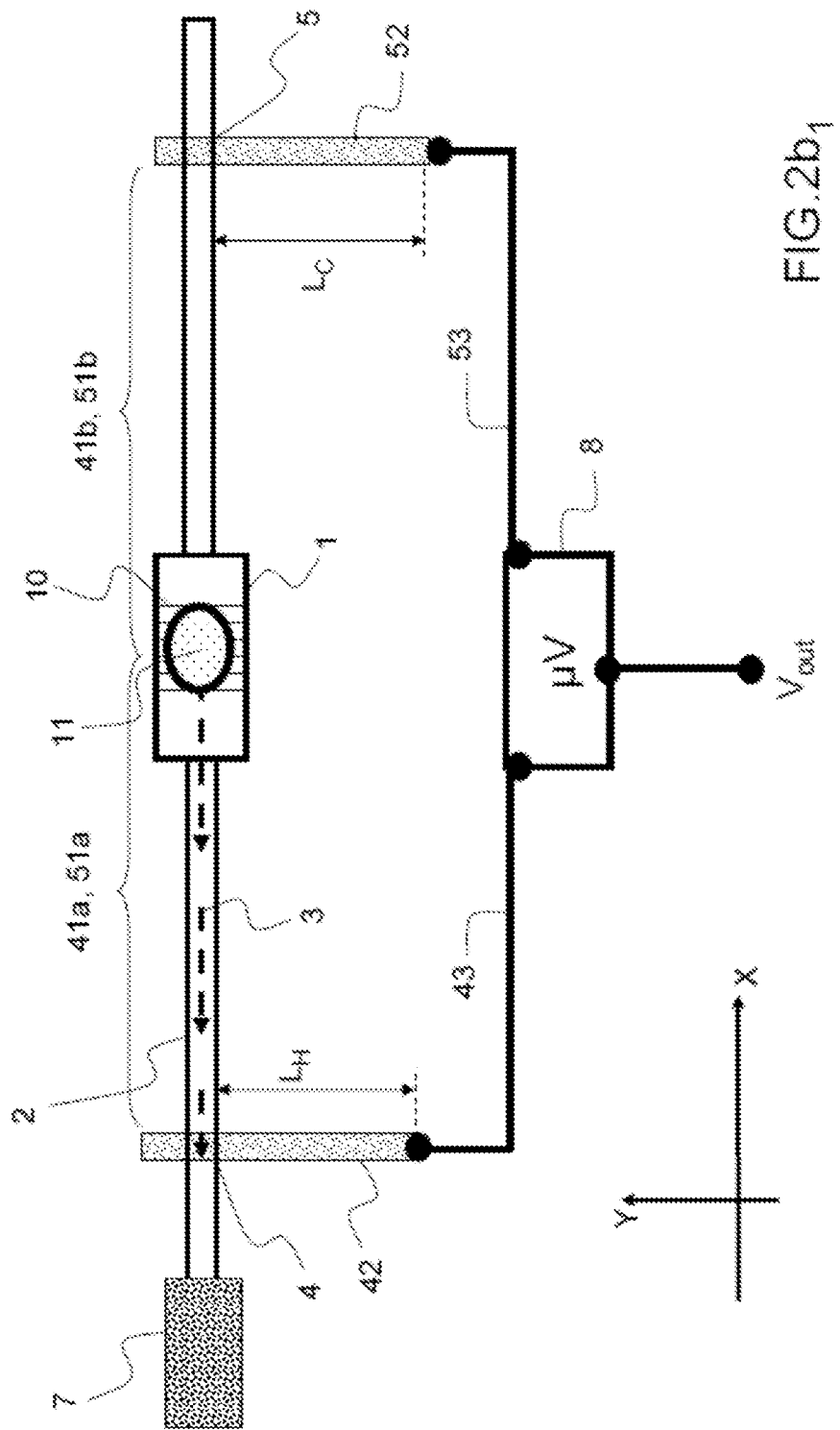

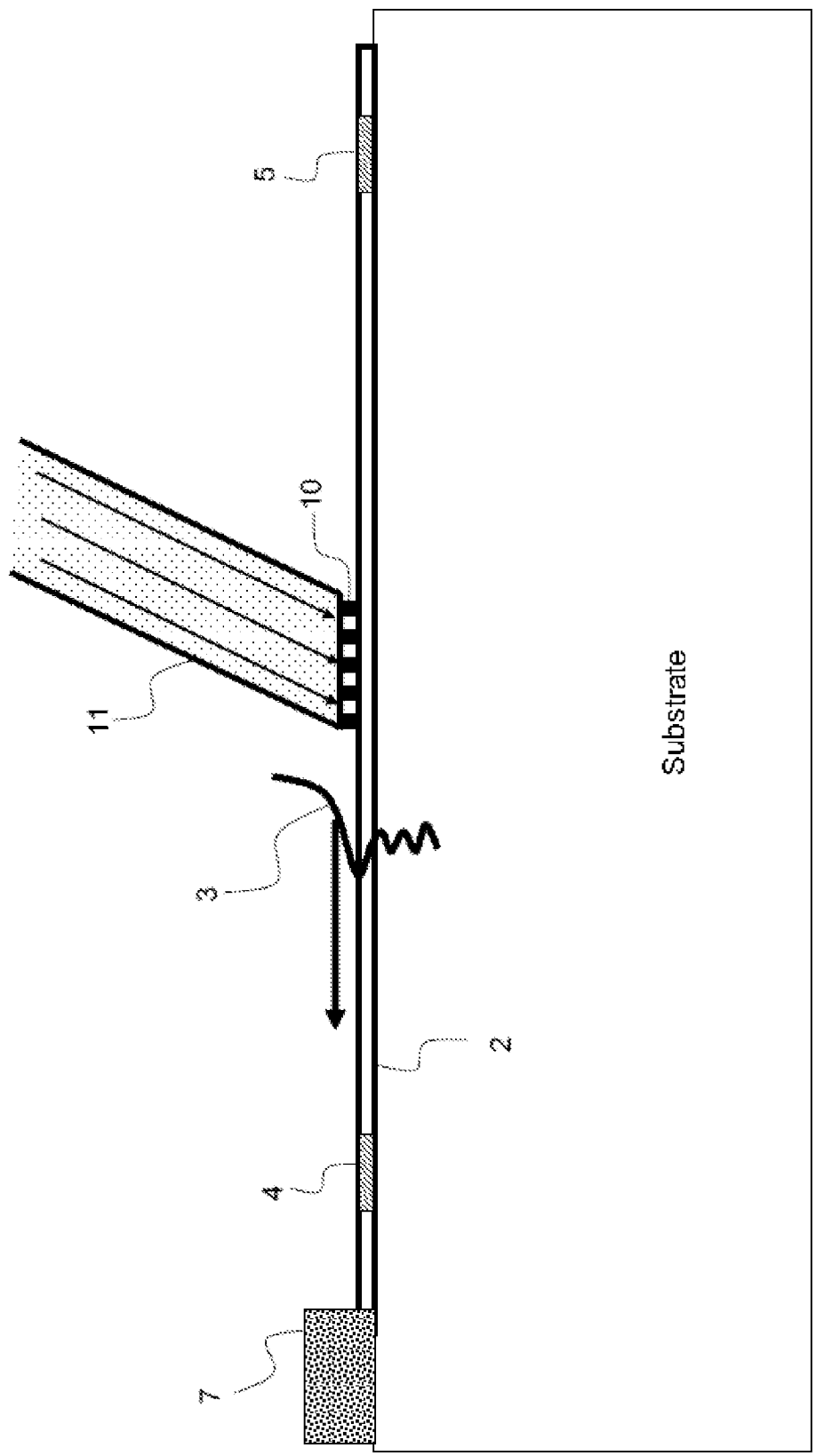

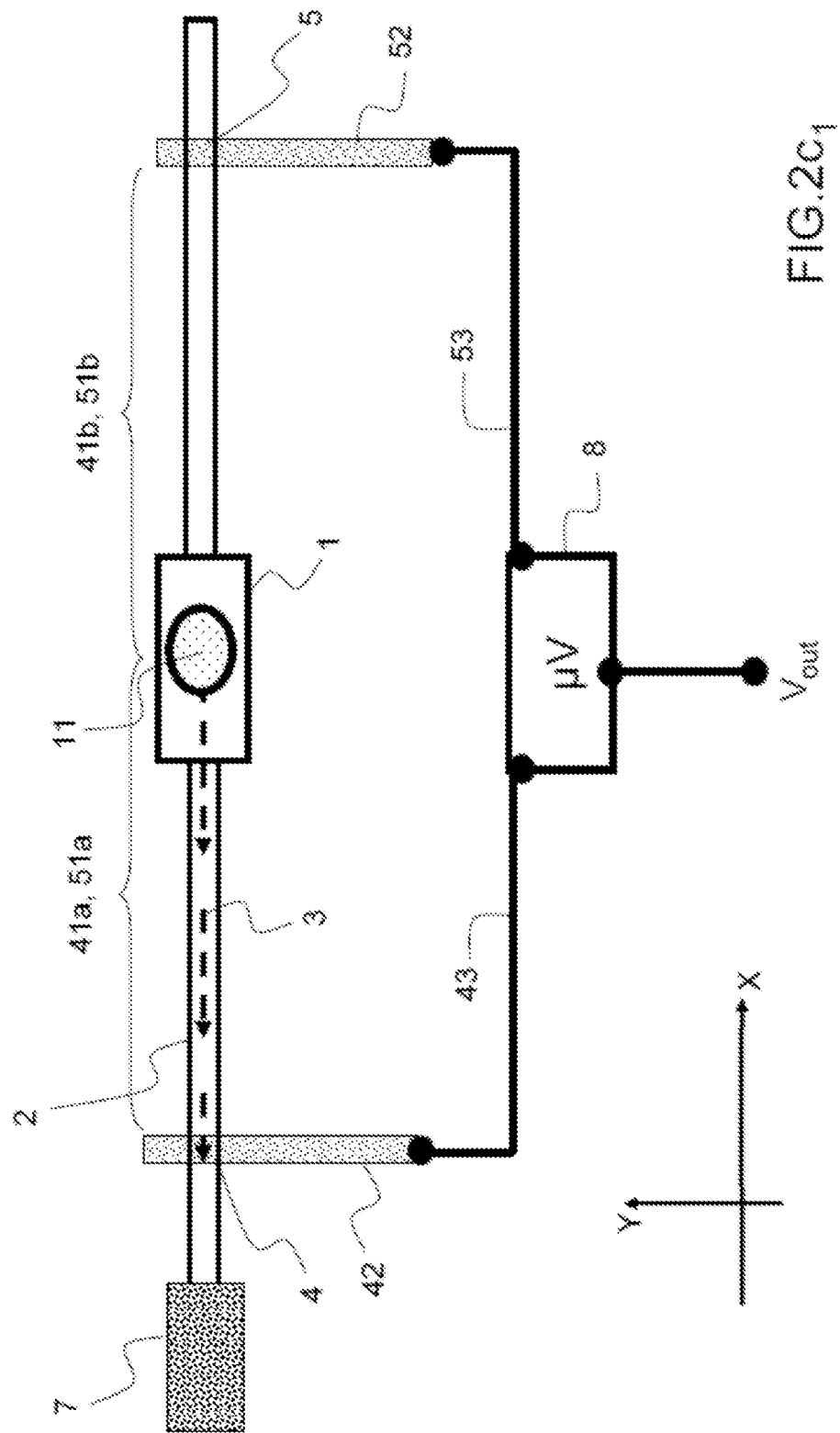

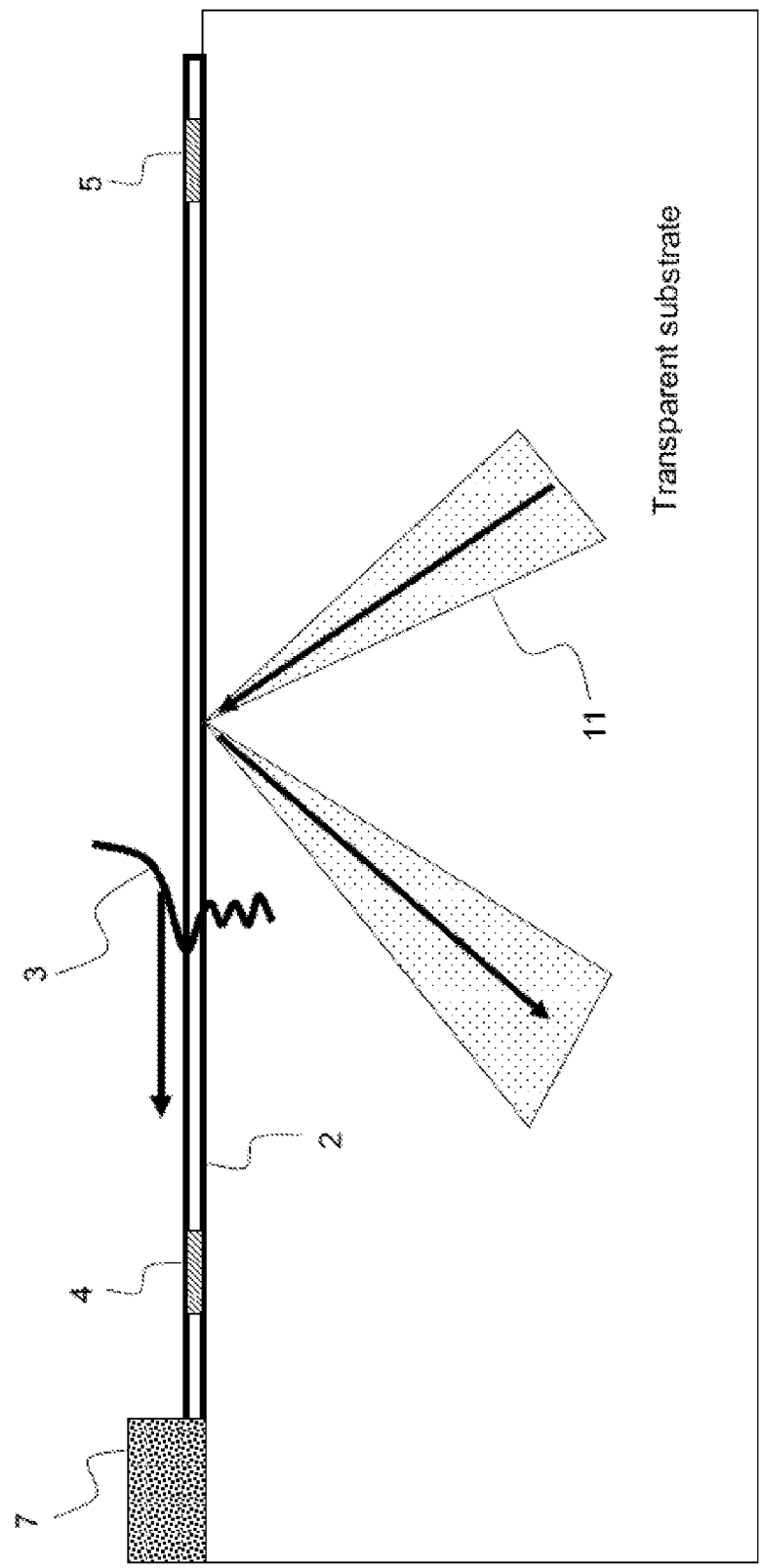

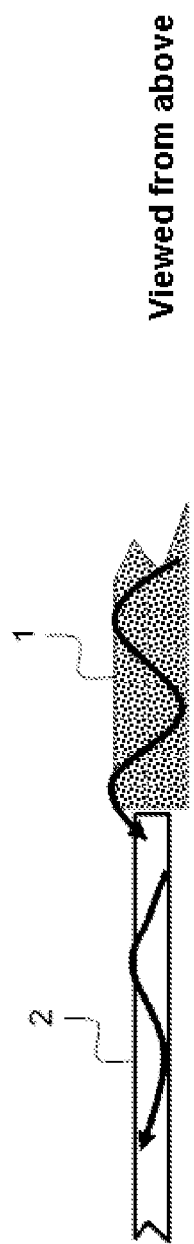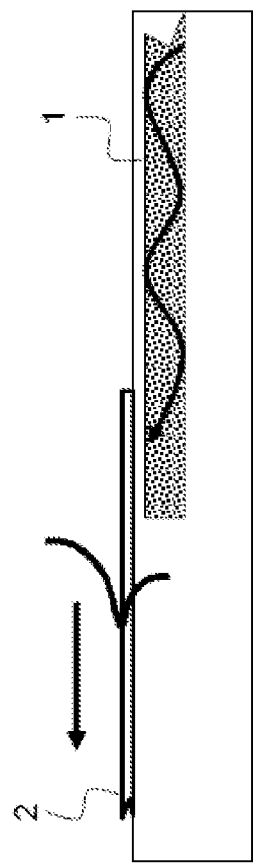
FIG.2e₁

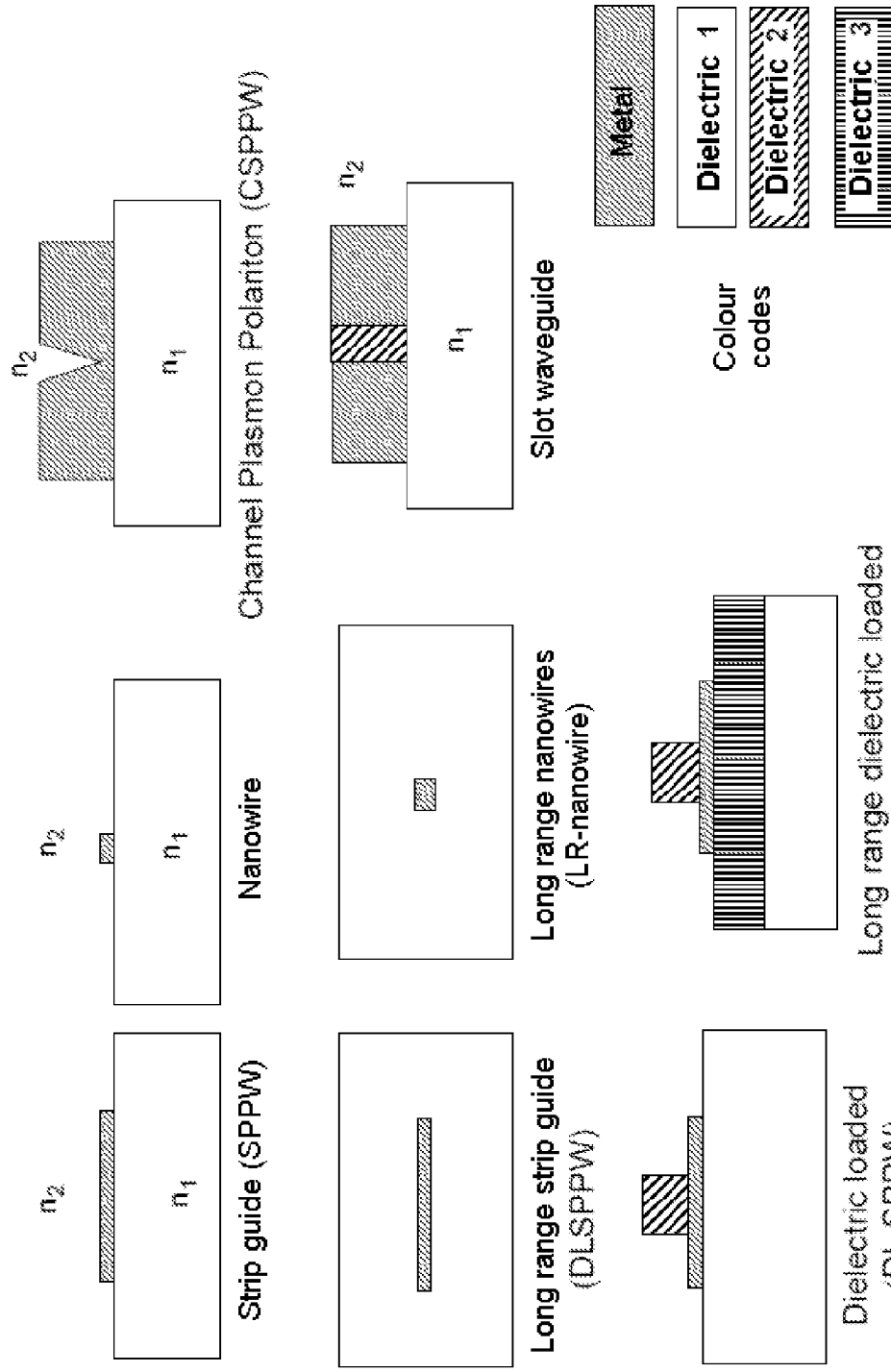

THERMOELECTRIC COMPONENT WITH PLASMONIC GUIDE, INTEGRATING A DEVICE FOR MEASURING THE POWER COUPLED IN THE GUIDED MODE

CROSS-REFERENCE TO RELATED APPLICATION

This application claims priority to foreign French patent application No. FR 1154393, filed on May 19, 2011, the disclosure of which is incorporated by reference in its entirety.

FIELD OF THE INVENTION

The field of the invention is that of plasmonic waveguides. The adjective "plasmonic" refers here to the concept of surface plasmon polariton, also shortened to "surface plasmon" in the literature.

BACKGROUND

The development of optical circuitry integrating plasmonic components has prompted a great deal of research work on a worldwide scale during the last decade. In this context and beyond simple passive plasmonic waveguides, integrated plasmonic sources and detectors with integrated plasmons are of genuine practical interest.

Very recently, plasmonic detectors based on the detection of a photocurrent in a semi-conductor have been described in the literature. The plasmonic guide serves as electrode for the measurement of the photocurrent. Such components are dedicated either to studies of phenomena in quantum optics, or to applications of plasmon-assisted integrated optics.

By way of example, it is possible to cite a type of plasmon-based integrated detector using a Schottky barrier but this mode of detection is necessarily limited to very attenuated guided plasmon modes propagating at the interface between a metal and a semi-conductor. An example of such a detector is described by A. Akbari, P. Berini, Appl. Phys. Lett., 95, 021104, (2009).

Moreover, from the point of view of a plasmonic component, the use of semi-conductors imposes draconian fabrication constraints (compatibility with CMOS fabrication processes), high cost and the necessity to work on specific substrates.

Another type of device relying on a thermo-resistive effect makes it possible to detect the power propagating along a plasmonic guide. An example of this type of device is presented by S. Bozhevolnyi, T. Nikolajsen, K. Leosson, in the publication "Integrated Power monitor for long range surface plasmon polaritons", Optics Communication, 255, 51, (2005). Such a detector requires a waveguide length sufficient to allow the detection of a variation in resistivity, thus rendering the miniaturization of the device difficult; moreover these detectors exhibit high response times of the order of a millisecond.

The measurement of the power conveyed by non-guided plasmon modes can, however, be carried out in a simple and effective manner by virtue of a thermoelectric scheme. The detection of the simple excitation of a plasmon mode by a thermoelectric system is for example described in U.S. Pat. No. 5,792,667: in this instance this entails detecting the excitation of a plasmon mode on an extended thin film for which no notion of guidance of the plasmon mode intervenes. It does not therefore entail detecting the power propagating along a plasmonic guide, the notion of guidance comprising the notion of lateral confinement of the plasmon mode. The same holds as regards the publication by R. A. Innes and J. R. Sambles, "Simple detection of surface plasmon-polaritons", Solid State Communications, 56, 493, (1985). In these two examples, the thermoelectric scheme is implemented to measure the optical reflectivity of the system integrating an extended thin metallic layer on which a surface plasmon is excited and not to obtain information on an arbitrary power associated with an optical or plasmonic guided mode.

SUMMARY OF THE INVENTION

The aim of the invention is to alleviate these drawbacks.

The present invention describes a thermoelectric component integrating:
  a waveguide supporting a plasmon mode, subsequently called a plasmonic guide,
  an exciter element for the guided plasmonic mode, which couples an optical power to the plasmonic guide,
  a device for measuring the optical power dissipated during propagation along the plasmonic guide.

The power measurement is based on a thermoelectric effect (also known as the Seebeck effect). The thermoelectric signal is obtained by virtue of one or more thermocouple junctions. Thermocouple junctions consist of the association of two metals or of the association of a metal and of a semi-conductor. In both cases, the plasmon mode considered propagates in guided form along a metallic electrode in such a way that the metal plays the dual role of plasmonic waveguide and of element of the measurement device.

During its propagation, a plasmon mode loses part of its energy in the form of ohmic losses causing the heating of the plasmonic guide and surrounding media. This heating is dubbed resonant hereinafter. The non-resonant heating of the component denotes the heating caused by any phenomenon other than solely the absorption of the guided plasmon mode during its excitation and its propagation.

The heating is detected by the measurement of the potential difference existing across the terminals of two electrodes of a given thermocouple junction or across the terminals of two electrodes belonging to different thermocouple junctions.

When a single thermocouple is implemented, the measurement is characteristic of the heating resulting from the resonant heating and the non-resonant heating of the component.

When the potential difference is measured between electrodes belonging to different thermocouple junctions and employing a precise arrangement of the thermocouple junctions and an initialization procedure described below, the measured electrical voltage is characteristic solely of the power conveyed by the guided plasmon mode and does not comprise any contribution arising from non-resonant heating of the plasmonic guide. Absolute measurement of the useful power exiting the plasmonic guide is then possible after a calibration procedure described below.

More precisely the subject of the invention is a thermoelectric component which comprises integrated into the component:
  a plasmonic waveguide,
  an exciter element for the guided plasmonic mode,
  a device for measuring the power dissipated during propagation along the plasmonic waveguide.

It is mainly characterized in that the measurement device comprises, associated with the plasmonic guide, a thermocouple junction with two electrodes, one of the electrodes including the plasmonic waveguide.

With this component, the useful signal has no exterior energy source to produce the useful signal since the thermocouple voltage results from the intrinsic properties (in this instance from the different Seebeck coefficients) of the materials making up the thermocouple junction. This characteristic distinguishes the component described here from the devices of the prior art for which the useful signal is obtained by using a voltage source both in the case of thermo-resistive devices and for semi-conductor-based detectors.

According to a characteristic of the invention, the plasmonic waveguide is a ring resonator, and the exciter element is a plasmonic waveguide or a conventional waveguide.

According to another characteristic of the invention, the thermoelectric component comprises a second plasmonic guide and a second thermocouple junction with two electrodes, one of the electrodes of this second junction including the second plasmonic waveguide, the first plasmonic guide being disposed on one branch of a Y junction, the second plasmonic guide being disposed on the other branch of the Y junction.

The component according to the invention advantageously relies on a particular disposition of the thermocouple junctions making it possible to select the thermoelectric signal originating exclusively from the resonant heating resulting from the absorption of the plasmon mode. This device allows the measurement of the guided plasmon power without tapping off useful power and furthermore enables detection of the plasmon mode in a zone of space where its amplitude may be negligible. The component may be implemented in the steady regime or in the time-dependent regime. Response times of less than 10 µs are achievable.

Preferably, the thermoelectric component comprises a second thermocouple junction with two electrodes, associated with the same plasmonic guide, one of these electrodes being common to the first thermocouple junction and including the plasmonic waveguide, the first junction termed the hot junction being intended to be in the path of the plasmonic guided mode. The second junction termed the cold junction being situated away from the path of the guided plasmon mode.

This configuration offers a solution for extracting a signal characteristic of the plasmon power alone while dispensing with any other form of heating of the guide. This refinement is not possible with the thermo-resistive configuration of the prior art cited in the preamble.

Furthermore it allows extreme miniaturization of the component since the thermocouple junction may in certain cases be limited to a surface area of a few hundred square nanometers ($nm^2$).

An optical component excited by the guide may also be integrated into the thermoelectric component.

The electrode including the plasmonic guide is advantageously metallic.

According to a variant, the exciter element for the guided mode comprises means for controlling its polarization.

This exciter element for the guided mode is for example a plasmonic or conventional (dielectric) optical waveguide, coupled to the plasmonic guide by coupling of "butt-coupling" type or by directional coupling in the plane, or by vertical directional coupling, the exciter waveguide being buried in a substrate.

This exciter element for the guided mode can also be a diffraction micro-grating whose lines are perpendicular to the longitudinal axis of the plasmonic guide, this grating being intended to be coupled to a laser beam at oblique incidence; the diffraction micro-grating causes the unidirectional excitation of the guided plasmon mode.

According to a characteristic of the invention, the micro grating is situated on the plasmonic guide at equal distance from the hot and cold junctions, and the measurement device comprises only a single detection device for detecting small potential differences.

This exciter element for the guided mode may be situated at an end of the guide and be a micro grating whose lines are perpendicular to the longitudinal axis of the guide and which is intended to be coupled to a focused laser beam, at normal incidence on the micro grating, the second part of the electrode being disposed in a direction in which the micro grating has no coupling efficacy.

This exciter element for the guided mode can also be a laser beam focused at super-critical oblique incidence through a transparent substrate.

According to another variant, the exciter element for the guided mode does not comprise any means for controlling its polarization.

In this case, the thermoelectric component comprises a heating element situated at the input of the plasmonic guide.

This heating element is for example a Pelletier element, or a metallic strip of micronic width or a focused incident light beam.

In certain cases, the power measurement device comprises a device for detecting small potential differences by thermocouple junction and linked to these two devices, a circuit for processing the potential differences obtained.

It is possible to supplement the exciter element with modulation means.

The invention also relates to a method of using a thermoelectric component such as described, characterized in that it comprises a step of initializing the measurement device by non-resonant heating of the plasmonic guide.

It comprises subsequent to the initialization step, a step of exciting a guided mode in the plasmonic guide.

Optionally, it comprises between the initialization step and the excitation step, a step of calibrating the measurement device.

In certain cases, the initialization step is carried out in a determined span of temperatures, and the step of exciting the guided mode is carried out for a temperature included in the said span of temperatures.

BRIEF DESCRIPTION OF THE DRAWINGS

Other characteristics and advantages of the invention will become apparent on reading the detailed description which follows, given by way of nonlimiting example and with reference to the appended drawings in which.

From one figure to another, the same elements are tagged by the same references.

DETAILED DESCRIPTION

The thermoelectric component comprises, integrated into the component:
- a plasmonic waveguide,
- an exciter element for the guided plasmonic mode,
- a device for measuring the power dissipated during propagation in the plasmonic waveguide.

Figure 1A:
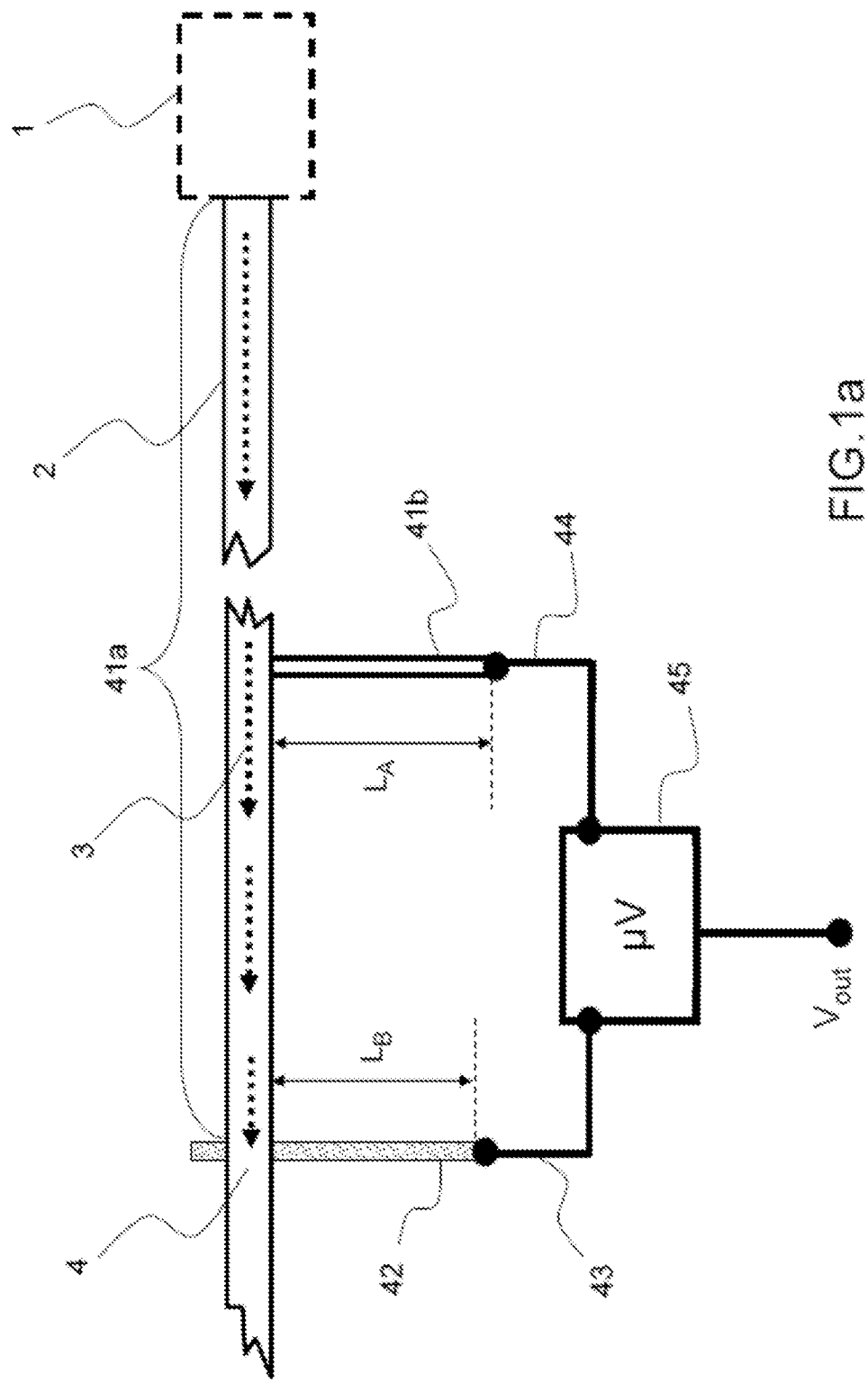
FIG. 1a schematically represents an exemplary embodiment of the invention with a single thermocouple junction, viewed from above, FIG. 1b schematically represents an exemplary embodiment of a resonance detector of a ring resonator with a single thermocouple junction, viewed from above, FIG. 1c schematically represents an exemplary embodiment of a Y junction with two plasmonic guides and two thermocouple junctions, viewed from above, FIG. 2a schematically represents an exemplary embodiment of the invention with two thermocouple junctions associated with a single plasmonic guide, viewed from above, FIG. 2b schematically represent another exemplary embodiment of the invention with two thermocouple junctions associated with a single plasmonic guide, with an exciter element comprising a micro-grating and a spot incident at oblique incidence, viewed from above (FIG. $2b_1$) and viewed in profile (FIG. $2b_2$), FIG. 2c schematically represent a third exemplary embodiment of the invention with two thermocouple junctions associated with a single plasmonic guide, with an exciter element comprising a spot incident at super-critical incidence, through a transparent substrate, viewed from above (FIG. $2c_1$) and viewed in profile (FIG. $2c_2$), FIG. 2d schematically represents a fourth exemplary embodiment of the invention with two thermocouple junctions associated with a single plasmonic guide, with an exciter element comprising a micro-grating and a spot incident at normal incidence, viewed from above, FIG. $2e_1$ illustrates several modes of excitation of the plasmonic guide by a waveguide, FIG. $2e_2$ presents various configurations of plasmonic waveguides with a strip, viewed in section, FIG. 3a schematically represents an exemplary embodiment of the invention with two thermocouple junctions associated with a single plasmonic guide, with a heating device, viewed from above, FIG. 3b schematically represents another exemplary embodiment of the invention with two thermocouple junctions associated with a single plasmonic guide, with a heating device, viewed from above.

According to a first embodiment of the invention, described in conjunction with FIG. 1a, the measurement device comprises a single thermocouple junction with two electrodes, associated with the plasmonic guide, one of the electrodes including the plasmonic waveguide.

This component makes it possible to perform just the measurement of the heating of the plasmonic guide without it being possible to separate in this measurement the contribution of the resonant and non-resonant heating.

The measurement relies on the following approach. The exciter element 1 excites the plasmonic guide 2. A fraction of the luminous power delivered by the exciter element is absorbed by the plasmonic guide without this absorption being related to the excitation of the plasmon mode. This heating is therefore dubbed non-resonant. A part of the luminous power delivered by the exciter element is coupled to the plasmon mode 3.

This mode which propagates along the guide loses a part of its energy in the form of heat, the latter causing the resonant heating of the guide. These two types of heating give rise to a potential difference across the terminals of the thermocouple junction 4. This thermocouple junction 4 comprises two different nature electrodes (two different metals, or one metal and one semi-conductor, etc.). An electrode 41 of a material A is composed of two parts, one part 41a being the guide 2, and another part 41b in which no guided mode propagates. Electrical continuity between the part 41a, that is to say the guide 2, and the part 41b of the electrode 41, must be ensured. Ideally, the part 41b is made of the same material as the part 41a, in this instance the material A but it may be from a different material. The other electrode 42 from a material B is connected to the plasmonic guide, that is to say to the part 41a of the electrode.

The electrodes 41b, 42 of the thermocouple junction are connected to the device 45 for detecting low voltages by electrical connections 43, 44 composed of a material that may be different from the materials A or B. The electrical connections between the device 45 for detecting low voltages and the electrode 42, or between the device 45 for detecting low voltages and the electrode 41b are not necessarily made of the same material. The length of the electrode 42 equal to the distance between the plasmonic guide 2 and the electrical connection 43 is denoted $L_B$, and the length of the electrode 41b equal to the distance between the plasmonic guide 2 and the electrical connection 44 is denoted $L_A$. In order to avoid a thermocouple effect at the level of the electrical junctions with the electrodes 41, 42, the distances $L_B$ and $L_A$ are preferably chosen to be fairly large (typically some hundred microns) so that the temperature at the level of the electrical junctions is equal to the ambient temperature. This is also valid in respect of the various embodiments described hereinafter.

The useful signal $V_{out}$ is obtained by way of a device for detecting low voltages 45 that may be a microvoltmeter, a differential amplifier, etc, delivering a signal proportional to the potential difference between the electrode 41 and the electrode 42.

Figure 1B:
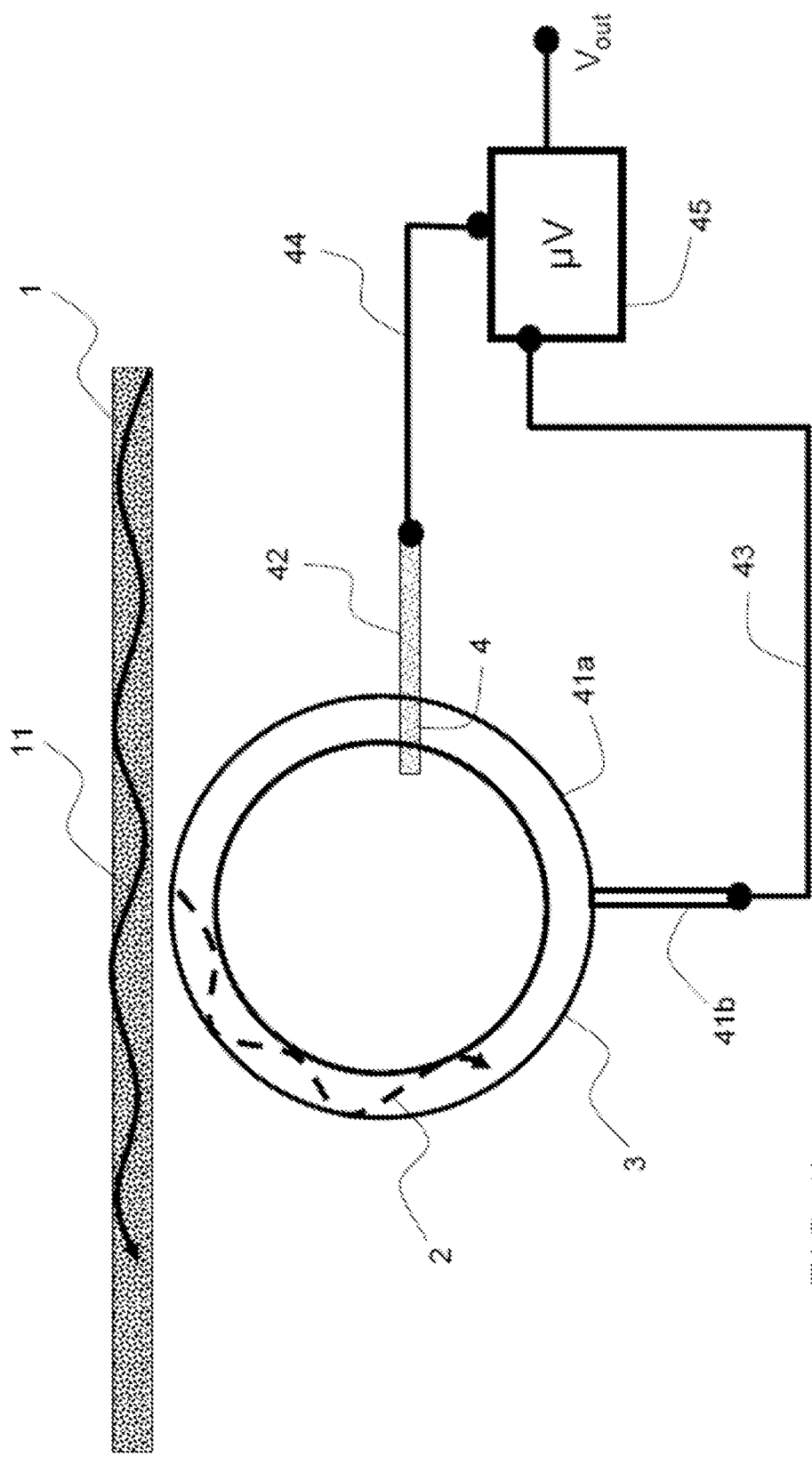

This embodiment is for example applied to a resonance detector, an example of which is represented in FIG. 1b.

An exciter element 1, here a plasmonic or conventional bus guide 1, in which a guided mode 11 propagates, makes it possible to excite a plasmonic guide 2, in this instance a for example ring or linear plasmonic resonator according to a configuration of Fabry-Perot type over an extended wavelength region. For a wavelength satisfying the resonance condition of the resonator 2, the energy accumulates in the resonator 2. On account of the ohmic losses of the guided plasmon mode 3, this energy accumulation is accompanied by heating of the resonator detected by the thermocouple junction 4 and by the device for detecting low voltages 45. Thus, the resonance of the resonator is manifested through an increase in the absolute value of the thermocouple voltage. The two electrodes of the thermocouple junction 4 are on the one hand the electrode 42 from a material B, on the other hand the electrode 41 from a material A, in two parts, the part 41a consisting of the resonator 2 and the part 41b in which the guided mode does not circulate. The geometry of the thermocouple junction 4 of the figure, represented by the intersection of a strip (electrode 42) and of the ring of the resonator, is merely indicative; the efficacy of the detection is all the greater when the thermocouple junction is distributed over the whole of the surface of the resonator, that is to say when the electrode 42 comprises two parts, a straight segment (the reference 42 in the figure) and a ring part (the resonator 2).

Figure 1C:
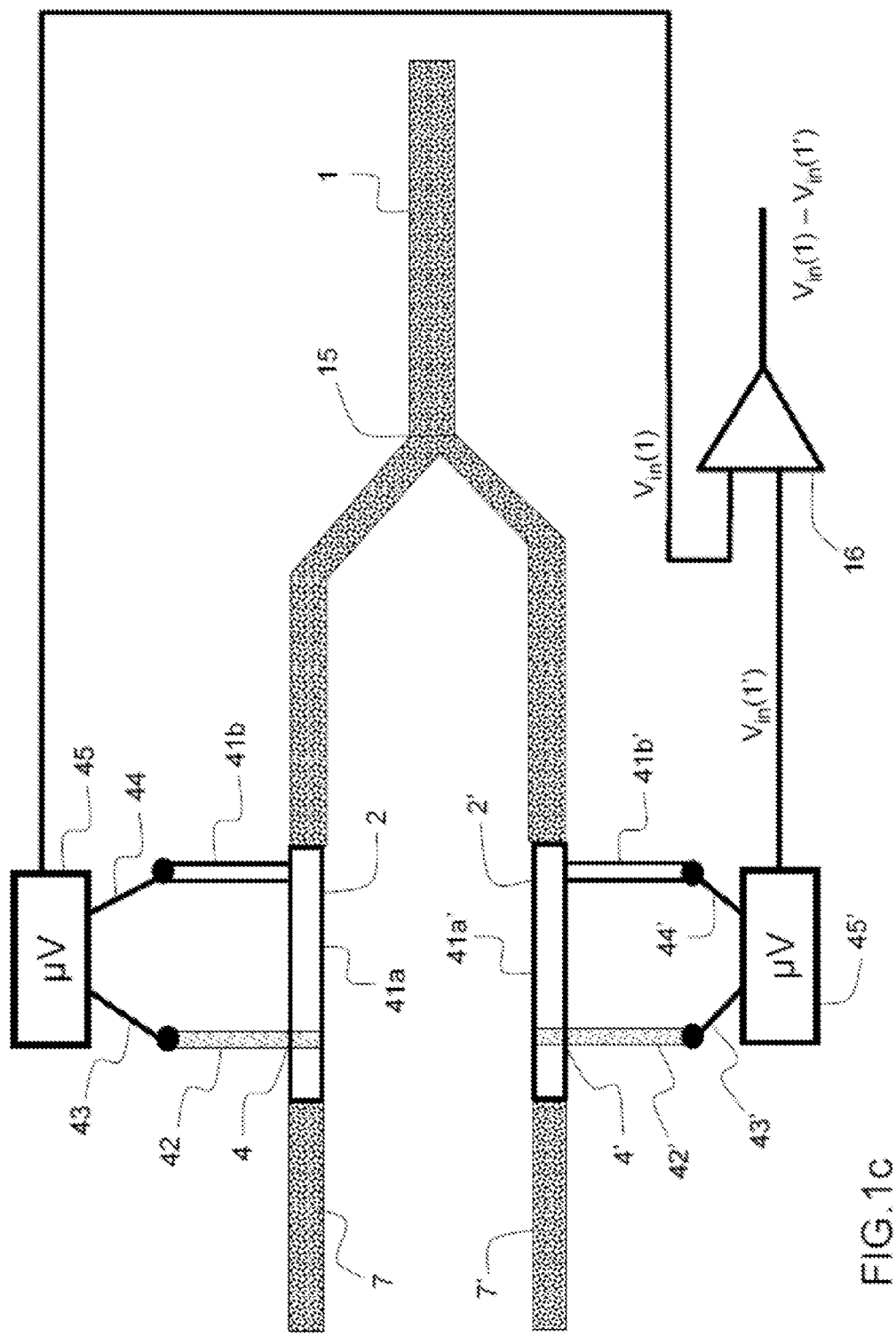

Another exemplary application of this first embodiment, described in conjunction with FIG. 1c, is the detection of an imbalance in a Y junction, each branch of the Y junction comprising a component according to this first embodiment which integrates a plasmonic or conventional output guide 7, 7'.

This second example shows a system comprising an exciter element 1 (for example a plasmonic or conventional waveguide) which is split by means of a splitter 15 into two branches, two thermocouple junctions 4 and 4' but also two plasmonic guides 2 and 2'. There is therefore indeed a thermocouple junction per plasmonic guide and the context is indeed therefore that of a simple measurement of the heating of each plasmonic guide. The voltage $V_{in}(\mathbf{1})$ is produced by the thermocouple junction 4 whose two electrodes are on the one hand an electrode 42 from a material B and an electrode from a material A, in two parts, a part 41a which is the guide 2 and a part 41b in which the mode does not circulate. The voltage $V_{in}(\mathbf{1'})$ is produced by the thermocouple junction 4' with two electrodes 42' on the one hand and 41a'-41b' on the other hand. Each of these two voltages is characteristic of the heating of the plasmonic guides 2 and 2' and therefore of the power propagating in each branch of the beam splitter. The signal $V_{in}(\mathbf{1})$-$V_{in}(\mathbf{1'})$ measured by the device 16 is therefore characteristic of the difference in power propagating in each branch of the splitter. Here again, the geometry of the thermocouple junctions may be different. In particular, it is possible to consider a configuration where the material B of the electrodes 41b and 41b' extends over the whole of the length of the plasmonic guides 2 and 2'.

As has just been seen, the excitation of a guided mode in the plasmonic guide causes inevitable non-resonant heating resulting from the simple absorption of the incident light (originating from a waveguide or from a focused light spot) without associated plasmon excitation and on the other hand resonant heating produced by the absorption of the plasmon mode during its propagation; but the respective contributions of these two types of heating are not known.

The relative measurement of the power conveyed by the guided plasmon mode, by thermoelectric effect, is possible only on condition that it is possible to separate the two contributions causing the heating of the plasmonic guides: on the one hand the resonant heating and on the other hand the non-resonant heating. By relative measurement is meant here the detection of a thermoelectric signal varying in proportion to the power conveyed by the plasmon mode, although without it being possible to ascribe a value of guided power (in Watts) to the value of the thermocouple potential difference measured (in Volts). It is however noted that the absolute measurement of the power conveyed by the plasmon mode is possible at the price of a calibration procedure making it possible to correlate the value of the thermocouple voltage characterizing solely the resonant heating of the guide with a value of power reaching the end of the plasmonic guide. The calibration procedure uses for example a photodiode integrated into the end of the plasmonic guide. This photodiode then playing the role of the excited optical component denoted 7 in the various figures. For a given type of plasmonic guide and a determined configuration of the thermocouple junctions, this calibration procedure makes it possible to establish a correlation between a value of thermocouple voltage (in Volts) characterizing solely the resonant heating of the plasmonic guide and a value of the power transmitted along the plasmonic guide (in Watts). Thus for a detection configuration identical to that for which the calibration procedure will have been carried out, solely the value of the thermocouple voltage characterizing the resonant heating of the guide makes it possible to deduce the power (in Watts) reaching the end of the plasmonic guide. The detection of a thermocouple voltage characterizing solely the resonant heating of the guide demands an initialization procedure described hereinbelow and affording access to a relative measurement of the power conveyed by the plasmonic guide.

Described here is an embodiment of the invention making it possible to obtain the relative measurement of the power conveyed by the plasmon mode. This approach applies notably to thermoelectric component configurations furthermore integrating an optical component excited by the guided mode propagating in the plasmonic guide; this component is typically a dielectric waveguide, plasmonic waveguide or the like. This is rendered possible by the fact that the relative measurement of the power conveyed by the plasmon mode is carried out without tapping off useful power.

According to this embodiment, the measurement device comprises two thermocouple junctions 4, 5 with two electrodes, each junction being associated with the same plasmonic guide 2, and these two junctions sharing one and the same electrode, the one which includes the plasmonic waveguide. The procedure for measuring the power of the guided plasmon mode then comprises two steps: an initialization step consisting in eliminating from the thermoelectric signal the contribution of the non-resonant heating and then a step of measuring the resonant heating that may be ascribed to the absorption of the power conveyed by the plasmon mode. It is not indispensable to undertake an initialization each time that the measurement step is carried out; the initialization remains valid for several measurements.

The separation of the two contributions (non-resonant heating and resonant heating) may be carried out in several ways depending on whether the polarization of the light source allowing the excitation of the plasmon mode can be controlled so as to prohibit or permit this excitation.

According to a first variant, it is possible to control the polarization of the exciter element and thus choose it so that the guided plasmon mode 3 is or is not excited.

The procedure for relative measurement of the power of the guided plasmon mode in this case is the following.

During the initialization step, the polarization is firstly adjusted in such a way that the incident electric field does not allow the excitation of a guided plasmon mode, that is to say is devoid of any field component allowing the excitation of the guided plasmon mode 3. Usually, this situation is obtained for a transverse electrical polarization TE, however for certain particular plasmonic waveguides supporting "channel plasmon polaritons" for example it is the TM polarization which ought to be chosen at this stage. In this configuration, the heating of the plasmonic guide 2 is caused by the absorption of the incident light without this heating being related to the excitation of the plasmon mode 3. It is therefore non-resonant heating. The aim of this initialization procedure is to establish a correction of the measured thermocouple voltages so as to separate the contribution of the resonant and non-resonant heating of the plasmonic guide.

Figure 2A:
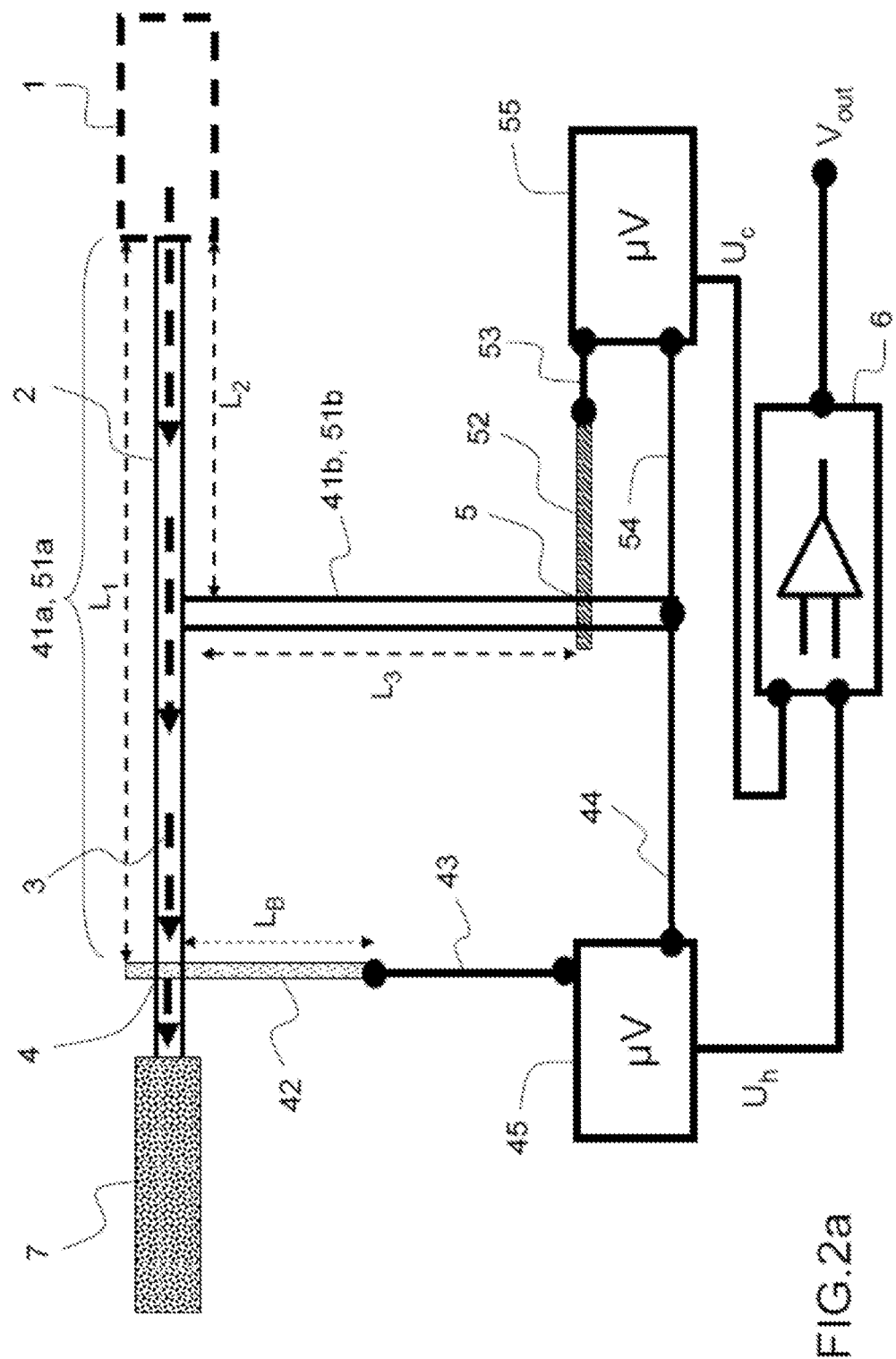

According to a first embodiment of this variant, described in conjunction with FIG. 2a, the measurement device comprises two devices 45, 55 for detecting low voltages which make it possible to measure the voltages $U_h$ and $U_c$ across the terminals of the hot 4 and cold 5 thermocouple junctions respectively, and an integrated circuit 6 for processing the voltages $U_h$ and $U_c$ to which the two devices for detecting low voltages are linked.

By way of indication, the circuit 6 for processing the voltages may be a circuit carrying out the operation $V_{out}=U_h-aU_c+V_{offset}$ with a an amplification coefficient and $V_{offset}$ a voltage offset that may be positive or negative.

The thermocouple junction 4 is termed hot since it is in the path of the guided mode 3, the thermocouple junction 5 being termed cold since it is not in the path of the guided mode 3. The two electrodes of the thermocouple junction 4 are on the one hand the electrode 42 from a material B, and on the other hand the electrode 41 from a material A in two parts. The electrode 42 is connected to the guide 2 and to an electrical connection 43 linked to the device 45; the electrode 41 in two parts 41a which is the guide 2 and 41b in which the plasmon mode does not circulate, this part 41b being connected to the device 55 by an electrical connection 44. The two electrodes of the thermocouple junction 5 are on the one hand the electrode 52 from a material D, and on the other hand the electrode 51 from a material A in two parts. The electrode 52 is connected to the guide 2 and to an electrical connection 53 linked to the device 55; preferably the material D is the same as the material B. The electrode 51 is common to the thermocouple junction 4; this is why the references 51a, 51b designate the same elements as the references 41a and 41b. The part 51b (=41b) is connected to the device 55 by an electrical connection 54.

The initialization of the power measurement device consists in determining the law which relates the voltages $U_h$ and $U_c$ when the heating of the plasmonic guide is purely non-resonant (therefore in the absence of guided plasmon mode). This law must be obtained over a span of non-resonant powers which contains the estimated value of the non-resonant heating during the excitation of the plasmon mode.

More precisely, the initialization procedure is begun with the recording of the voltages $U_h$ and $U_c$ for non-resonant powers varying between 0 and $P_{nr}(\max)$. Thus a law $f_h$ and $f_c$ is determined for each of the voltages in the form $U_h=f_h(P_{nr})$ and $U_c=f_c(P_{nr})$. Knowing these two laws, it is easy to determine the law g such that $U_h-g(U_c)=0$ for all values of $P_{nr}$ varying between 0 and $P_{nr}(\max)$. By way of indication, this law could be simply linear and characterized by the coefficients a and $V_{offset}$ as described previously. This law g having been determined, it is possible to pass to the next step, modifying the polarization in such a way that the guided plasmon mode is actually excited so as to then be able to measure the power in the presence of the guided plasmon mode. In this case the voltages $U_h$ and $U_c$ can also be denoted in the form $U_h=U_{hspp}+U_{hnr}$ and $U_c=U_{cspp}+U_{cnr}$ where the contributions $U_{xspp}$ and $U_{xnr}$ (with x=h or c) are respectively related to the resonant heating ("spp" being the acronym standing for the expression "Surface Plasmon Polariton") and non-resonant heating. The relative values of each of these voltages are unknown; however if we apply the correction law g we have:

$$U_h-g(U_c)=U_{hnr}+U_{hspp}-g(U_{cnr}+U_{cspp})=U_{hspp}-g(U_{cspp})+U_{hnr}-g(U_{cnr}).$$

Now, by virtue of the non-resonant initialization obtained with the aid of the adjustment carried out by the circuit, we have $U_{hnr}-g(U_{cnr})=0$, this holding solely for the non-resonant contributions. Indeed, for the resonant contributions, a different temperature distribution from the non-resonant case is expected because of the presence of the guided plasmon mode. It follows from this that the voltage difference $U_h-g(U_c)=U_{hspp}-g(U_{cspp})$ is specific to the guided plasmon mode. The thermoelectric signal thus obtained is therefore indeed characteristic of the power absorbed during the propagation of the plasmon mode.

This configuration is all the more efficacious when the voltages $U_{hspp}$ and $U_{cspp}$ are as different as possible. This occurs on condition that $L_2$ is as small as possible.

Illustrated in FIG. $2e_1$ are various types of excitation of the plasmonic guide 2 by a waveguide 1 according to a:

coupling of "butt-coupling" type, the guide 2 being in the prolongation of the guide 2,
coupling of directional-in-the-plane coupler type, the guide 1 being in part on the side of the guide 2,
coupling of vertical directional coupler type, the guide 1 being a guide buried in a transparent substrate on which is deposited the plasmonic guide 2 which overlaps in part the guide 1.

Figure 2D:
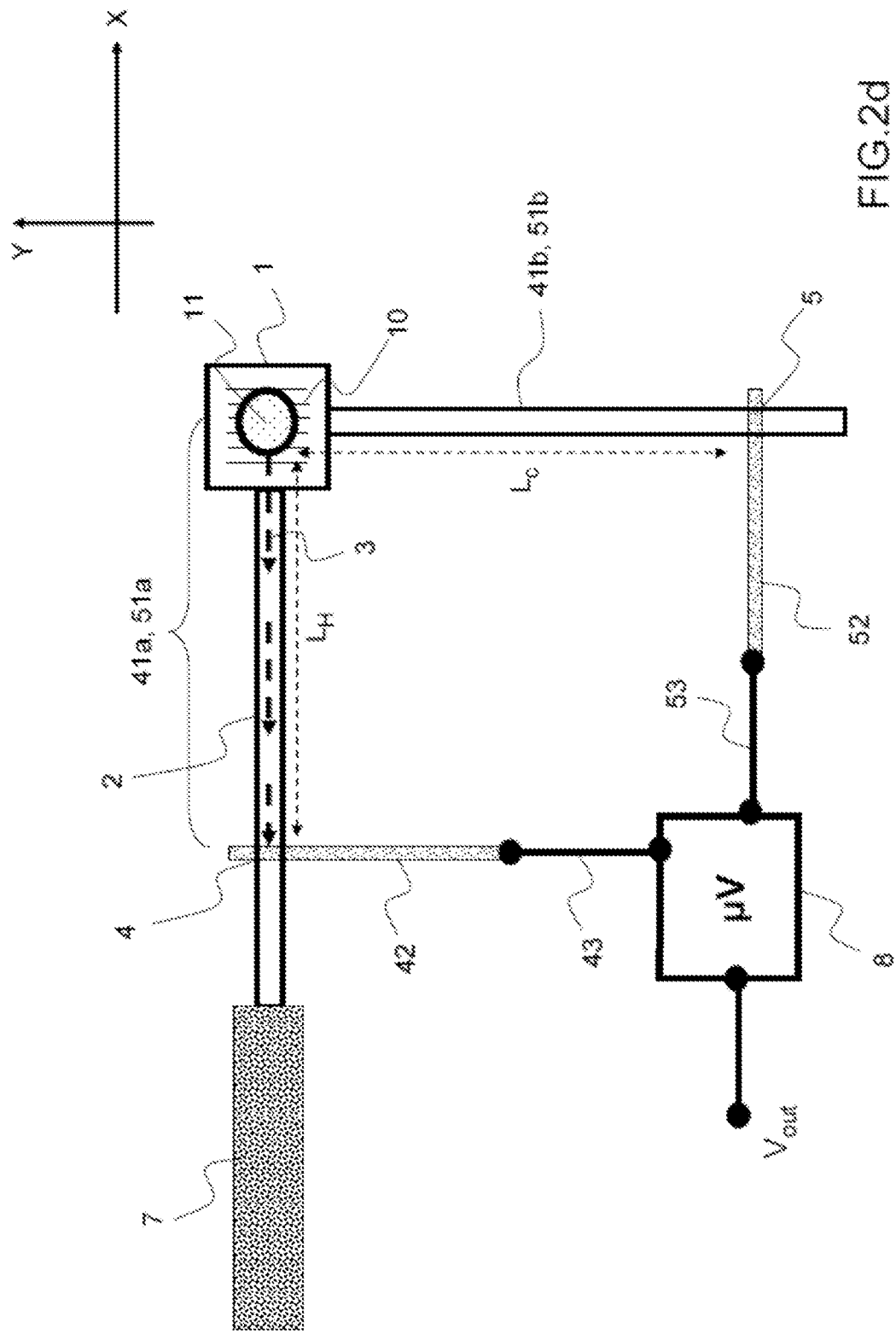

According to a second embodiment of this variant, described in conjunction with FIGS. 2b, 2c and 2d, it is possible to dispense with the integrated circuit 6 for processing the voltages $U_h$ and $U_c$. Accordingly, it is necessary that the potential difference between the electrodes 42 and 52 be zero as soon as the heating of the guide is purely non-resonant. The measurement device comprises a single device for detecting low voltages 8 making it possible to measure the voltages $U_h$ and $U_c$ across the terminals of the hot 4 and cold 5 thermocouple junctions, more precisely across the terminals of the electrodes 42 and 52; it no longer comprises any circuit 6 for adjusting the voltages. Without being detrimental to generality, it is assumed in these examples that the hot and cold thermocouple junctions are obtained on the basis of electrodes 42 and 52 of the same nature (=of the same material B).

In this case a thermocouple voltage is measured across the terminals of the electrodes 42, 52 of the same nature; this voltage U is in fact the voltage $U=U_h-U_c$. During the initialization phase (non-resonant excitation with a TE polarization, which diffuses its heat along the common electrode 41, 51 towards the two thermo junctions, hot 4 and cold 5) the excitation spot 11 is initially in a position along X such that $U_h=aP_{nr}$ and $U_c=bP_{nr}$ where a and b are a priori different coefficients. The phase of centring the spot 11 makes it possible precisely to adjust the coefficients a and b in such a way that they are equal. It is noted that as soon as the spot 11 is centred in the X direction between the two junctions 4 and 5, the equality of the coefficients a and b is true whatever the incident non-resonance power so that in these particular typical cases it is not necessary to consider a span of incident non-resonant powers.

As soon as this adjustment of the spot has been carried out, the second step is undertaken, changing the incident polarization in such a way that the excitation of the plasmon mode is effective. In this case we have: $U_h-U_c=U_{hspp}+aU_{hnr}-(U_{cspp}+aU_{cnr})=U_{hspp}-U_{cspp}$ which is a quantity characteristic of the guided plasmon mode.

The examples of FIGS. 2b and 2c differ solely by their exciter element 1.

In the example of FIG. 2b, the guided mode 3 is excited by illumination 11 at oblique incidence of a micro-grating 10 whose lines along Y are perpendicular to the longitudinal axis of the guide 2. Oblique incidence allows unidirectional excitation of the guided plasmon mode 3.

In the example of FIG. 2c, the guided mode 3 is excited by illumination 10 at incidence in the Kretschmann-Raether configuration (Illumination at super-critical incidence through a transparent substrate with reflection at the interface between the substrate and the guide 2; there is no micro-grating). Oblique incidence allows unidirectional excitation of the guided plasmon mode 3.

In the example of FIG. 2d, the guided mode 3 is excited by illumination 11 at normal incidence of a micro-grating 10 whose lines along Y are perpendicular to the longitudinal axis of the guide. In this case, there cannot be any unidirectional excitation of the plasmon guided mode 3 (that is to say only towards the hot junction 4); the cold junction cannot therefore be disposed in alignment (along the X direction) with the plasmonic guide. On the contrary in this case the cold thermocouple junction 5 is disposed in a direction in which the micro grating 10 has no coupling efficacy, for example at 90° to the propagation axis of the plasmonic guide 2 so that the plasmon mode cannot propagate in this direction. The measurement procedure is then the following. The polarization is fixed as TE that is to say in this case parallel to the lines of the grating, and the X and Y position of the incident spot 11 is adjusted in such a way that the signal $V_{out}$ provided by the device 8 for measuring the low voltages is zero. This adjustment is optimum if the hot 4 and cold 5 junctions are situated at identical distances $L_C$ and $L_H$ with respect to the micrograting 10. Once the adjustment of the incident spot 11 has been carried out, the polarization may be oriented perpendicularly to the lines of the grating thus causing the excitation of the guided plasmon mode 3. Under these conditions, and by adjusting the hereinabove described position of the spot, the signal $V_{out}$ is characteristic of the guided plasmon power.

According to a second variant, the polarization of the excitation source cannot be adjusted so as to prohibit the excitation of the plasmon mode. The measurement procedure described previously in conjunction with FIGS. 2a, 2b, 2c and 2d cannot be applied since it is not possible to have an excitation of the plasmonic guide which causes only non-resonant heating. In this case, a device 13 for local heating of the guide making it possible to simulate non-resonant heating, is added to the component described in conjunction with FIG. 2a. The heating device may be of diverse nature: it may be a Pelletier element, a simple metallic strip of micronic width as shown in FIG. 3a or even a focused incident light beam issuing for example from a laser diode as shown in FIG. 3b.

Figure 3A:
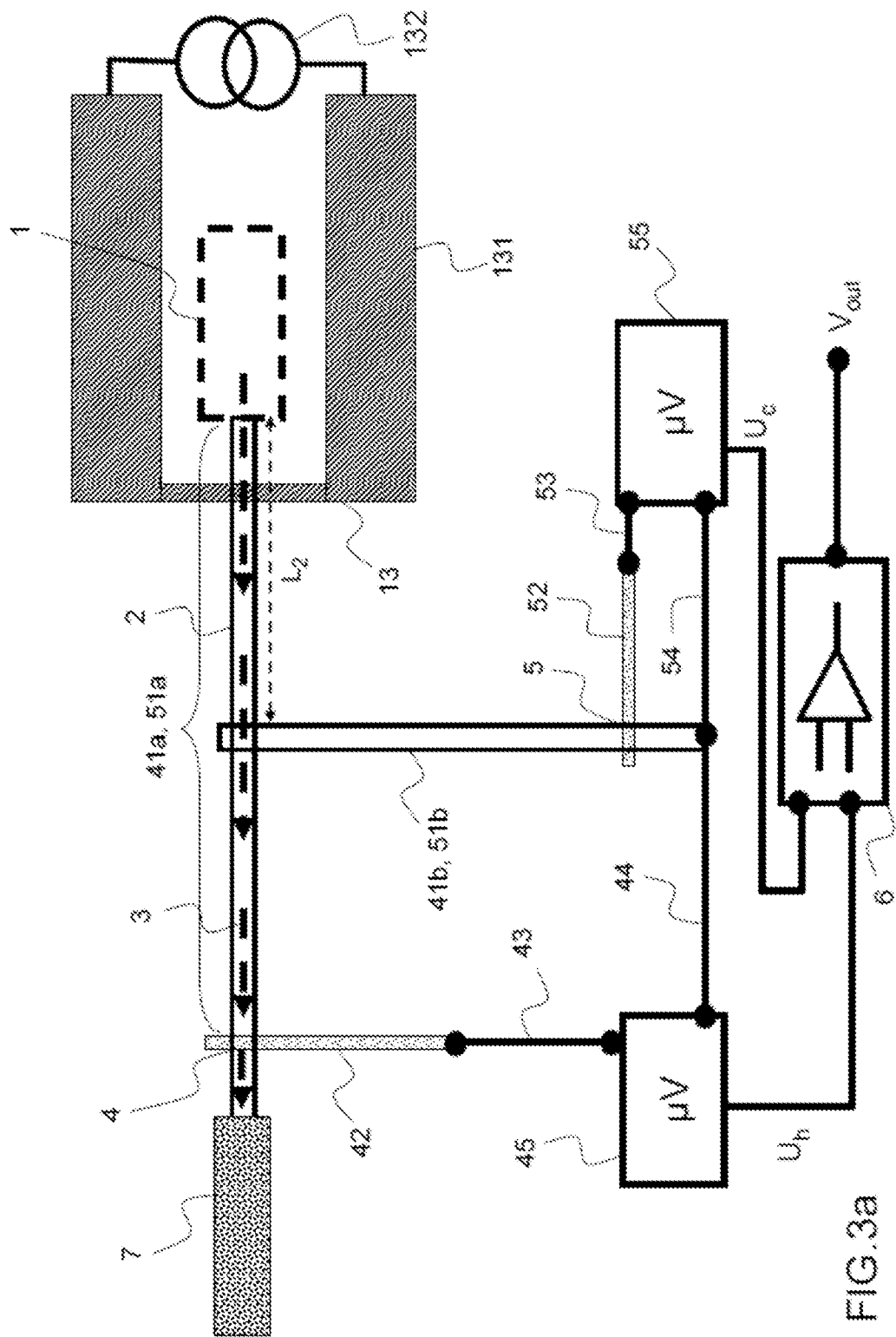

The measurement procedure using the configuration of FIG. 3a is very similar to that of FIG. 2a. Here, the non-resonant heating step is replaced with a step of heating the guide, carried out with the aid of the electrical heating device 13 which comprises a current source 132 which makes it possible to excite the heating element 131. Thus for given strengths of current passing through the heating element 131, the parameters of the integrated circuit 6 are adjusted in such a way that the output signal $V_{out}$ is zero. As soon as this adjustment phase has been carried out, the plasmonic guide 2 may be excited, the heating element 13 being off. The signal $V_{out}$ measured in this case is then characteristic of the guided plasmon power.

Figure 3B:
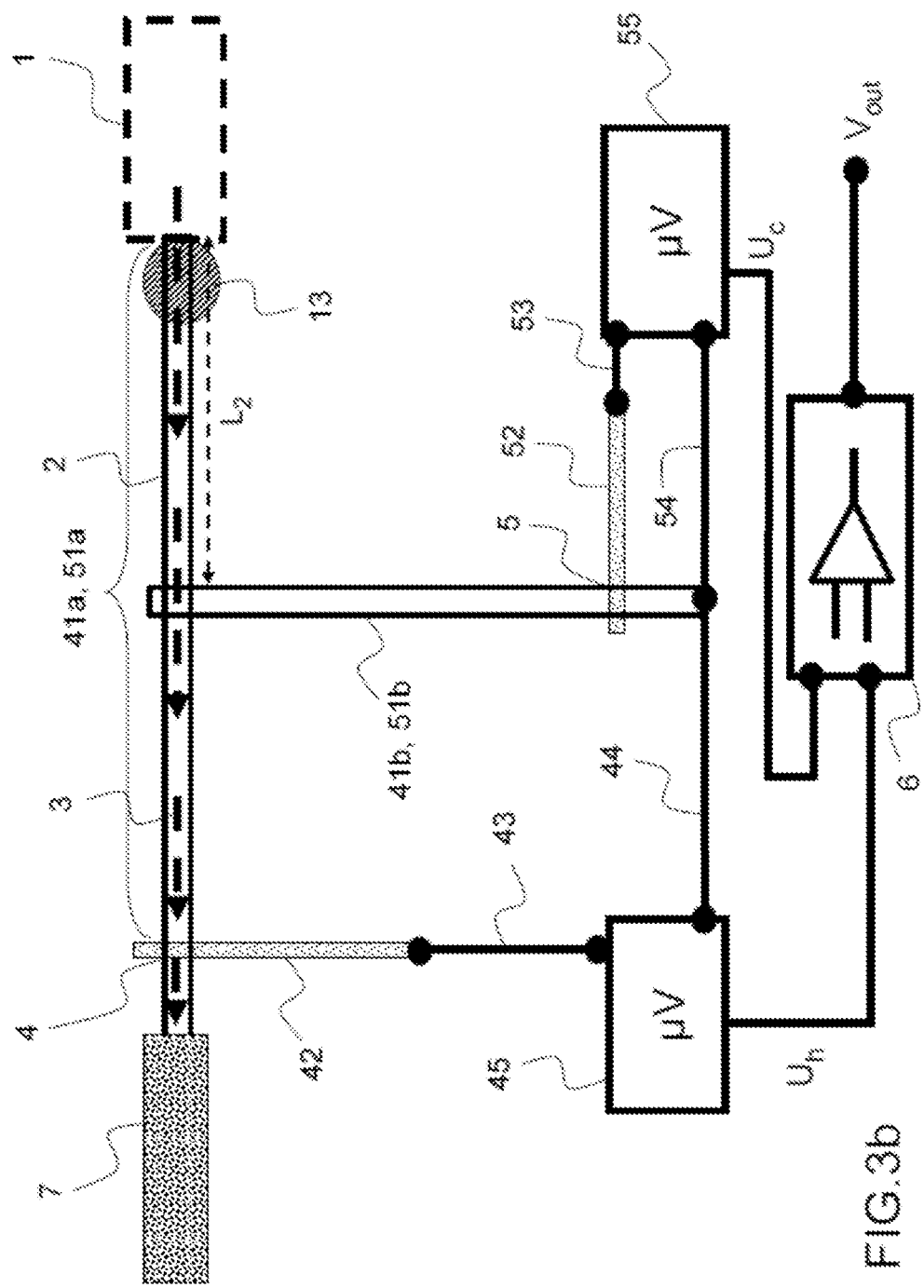

In the case of FIG. 3b, the electrical heating device of FIG. 3a is replaced with a focused incident light spot 13. This spot must be positioned at the input of the plasmonic guide 2 so as to produce non-resonant heating allowing the adjustment of the parameters of the integrated circuit 6.

These configurations (FIGS. 3a and 3b) are all the more efficacious when the voltages $U_{hspp}$ and $U_{cspp}$ are as different as possible. This occurs on condition that $L_2$ is as small as possible.

The component according to the invention is suited to plasmonic guides of a type termed strip guides, shown in FIG. $2e_2$ whether this be the:

- surface plasmon waveguide (acronym SPPW standing for the expression "Surface Plasmon Polariton Waveguide", presented in the publication by J. C. Weeber et al., Phys. Rev. B, 64, 045411, (2001)), obtained by depositing a thin metallic strip on a non-metallic substrate. The substrate possesses a different refractive index from the superstrate at the wavelength of the mode of the SPPW. The thickness E, the width (La) and the length (Lo) of the strip are such that E<<La<<Lo. The shape of the circuit traced by the strip is determined by the context of the application. The dimensions are adjusted so as to support a plasmon mode at the wavelength defined by the context of the application. The cross section of the plasmonic guide may be trapezoidal or rectangular. The propagation length along the strip is of the order 100 μm for the IR.
- plasmon nanowire which corresponds to a metallic wire deposited on a substrate, presented in the publication by J. C. Weeber et al., Phys. Rev. B, 9061, (1999). This configuration is distinguished from the SPPW guide in that its overall thickness (EHT) and its overall width (LHT) are of the same order of magnitude (EHT~LHT). The term nanowire distinguishes this configuration from a conventional metallic wire in that the shape of the cross section of the wire and the dimensions which define this shape are such that the wire supports a surface plasmon mode for a wavelength of an (optical) electromagnetic excitation relevant in the context of an application. Typically, these dimensions are smaller than a micrometer. The substrate possesses a different refractive index from the superstrate at the wavelength of the mode of the nanowire.
- the channel with surface plasmon polariton (CSPP acronym standing for the expression "Channel Surface Plasmon Polariton", presented in the publication by S. I. Bozhevolnyi, Nature, 440, 508-511, November 2005), which corresponds to a channel etched in a metallic support. This metallic support may be a hefty metallic substrate, a thin metallic film deposited on a substrate or a metal strip waveguide such as described for the SPPW guide. The substrate possesses a different refractive index from the superstrate at the wavelength of the mode of the CSPP.
- the plasmonic waveguide loaded with a dielectric (DL-SPPW acronym standing for the expression "Dielectric Loaded Surface Plasmon Waveguide") which corresponds to the SPPW to which is added a dielectric waveguide deposited on the metallic strip. The width of the dielectric waveguide is smaller than that of the strip which supports it. The substrate possesses a different refractive index from the superstrate at the wavelength of the mode of the DLSPPW. The cross sections of the dielectric guide and of the plasmonic guide are trapezoidal or rectangular.
- The long-range surface plasmon guide (LR-SPPW acronym standing for the expression "Long Range Surface Plasmon Polariton Waveguide") which corresponds to the SPPW modified in that the refractive indices of the substrate and of the superstrate are equal at the wavelength of the surface plasmon mode which then propagates much further than for the SPPW; the propagation length along the strip is of the order 1 to 2 mm for the IR.
- The long-range nanowire (LR-nanowire) which corresponds to the nanowire modified in that the refractive indices of the substrate and of the superstrate are equal at the wavelength of the surface plasmon mode which then propagates much further than for the nanowire.
- The "slot" waveguide which corresponds to a trench sliced in a metallic film, the refractive indices of the substrate, of the superstrate and of the space situated between the two metallic walls possibly being identical or different.
- The LR-DLSPPW guide, the acronym standing for the expression "Long Range Dielectric Loaded Surface Plasmon Polariton Waveguide", which corresponds to a dielectric layer of refractive index $n_2$ deposited on a substrate of refractive index $n_2 < n_1$. On the layer of index $n_2$ are successively deposited a thin metallic strip acting as plasmonic guide and then a second dielectric waveguide of index $n_3$. The cross sections of the various guides are trapezoidal or rectangular. The propagation length along the strip is of the order 1 to 2 mm for the IR.

A component according to the invention has been embodied according to the example of FIGS. $2c_1$ and $2c_2$ on the basis of a transparent glass substrate deposited on the hypotenuse of a right prism and connected to this prism by way of a liquid ensuring continuity of the refractive index between the substrate and the prism. The plasmonic guide (=part 41a, 51a) and the part 41b (or 51b) of the electrode in the form of a gold strip which has a thickness of 65 nm and a width of 3 µm, and the other electrodes 42, 52 in the form of nickel strips with a thickness of 38 nm and a width of 2 µm have been lithographed on the upper face of the substrate in contact with the air. The gold electrode comprises a widened central zone (designated launch zone hereinafter) on which the beam 11 will be focused. The zones where the gold electrode 41, 51 overlaps the nickel electrodes 42, 52 constitute the thermocouple junctions 4, 5 whose thermoelectric power is estimated at 22 µV K$^{-1}$ according to the tabulated values of the Seebeck coefficients for gold and nickel.

The focused beam 11 whose frequency corresponds to a wavelength in vacuo of 800 nm is obtained with the aid of a lensed optical fibre.

A device comprising a polarizer and a half-wave plate makes it possible to control the polarization of the incident beam.

The incident beam 11 being focused on the launch zone, for a TM (transverse magnetic) polarization of the incident beam (that is to say a linear polarization parallel to the plane of incidence), a plasmon mode confined to the interface between the gold and the air may be excited on condition that the mean angle of incidence of the beam is close to the critical angle of total internal reflection of the glass/air interface. The oblique incidence of the beam enables only unidirectional excitation of the plasmon mode (from right to left as shown in FIGS. $2c_1$ and $2c_2$). The plasmon mode excited on the launch zone is coupled to the guided plasmon mode 3 supported by the gold strip 2 and propagates as indicated hereinabove from right to left. It follows from this that the thermocouple junctions designate respectively the "hot" 4 and "cold" 5 thermocouple junctions. The nickel electrodes 42, 52 are contacted electrically with the aid of micro-tips 43, 53 connected to a differential amplifier 8 which makes it possible to measure the voltages across the terminals of the electrodes 42, 52 of the various thermocouple junctions 4 and 5.

The procedure used to effect a relative measurement of the plasmon power propagating along the gold electrode 41 is the following. The angle of incidence of the beam 11 is firstly adjusted in such a way that, for a TM incident polarization, the plasmon mode 3 may be excited. The polarization of the incident beam is then oriented in the TE direction (electric field perpendicular to the plane of incidence) and the thermocouple voltage is measured across the terminals of the two nickel electrodes 42, 52. This voltage is denoted $V_{Ni-Ni}$ hereinafter. For an arbitrary longitudinal position (that is to say along the X axis of the gold electrode) of the incident beam 11, the voltage $V_{Ni-Ni}$ is a priori nonzero. Indeed in such a case, the heating of the system resulting from the absorption by the gold layer of a fraction of the incident light produces different temperatures at the points 4 and 5 and consequently a nonzero voltage value $V_{Ni-Ni}$. The hot 4 and cold 5 thermocouple junctions having been disposed at equal distance from the centre of the launch zone, it is however possible to cancel the voltage $V_{Ni-Ni}$ measured under TE polarization by centring the incident spot 11 with respect to the two thermocouple junctions 4 and 5. The TE polarization giving rise only to non-resonant absorption of the incident light, the longitudinal centring of the incident spot therefore makes it possible to eliminate the contribution to $V_{Ni-Ni}$ of the "non-resonant" heating and to do so whatever the absorbed non-resonant power. The relative measurement of the plasmon power propagating along the guide is then obtained by orienting the incident polarization in the TM direction. For this polarization state, the excited plasmon mode propagates towards the hot electrode. In the course of its propagation, this mode is progressively absorbed giving rise to a non-symmetric temperature distribution with respect to the centre of the launch zone. This asymmetry is responsible for a nonzero voltage value $V_{Ni-Ni}$. On the basis of this analysis, it can therefore be concluded that on completion of the initialization procedure consisting here of an adjustment of the longitudinal position of the incident spot, the voltage $V_{Ni-Ni}$ measured under TM polarization is characteristic of the power coupled in the plasmon mode. The aim of the experiments which follow is to bolster this conclusion.

Figure 4B:
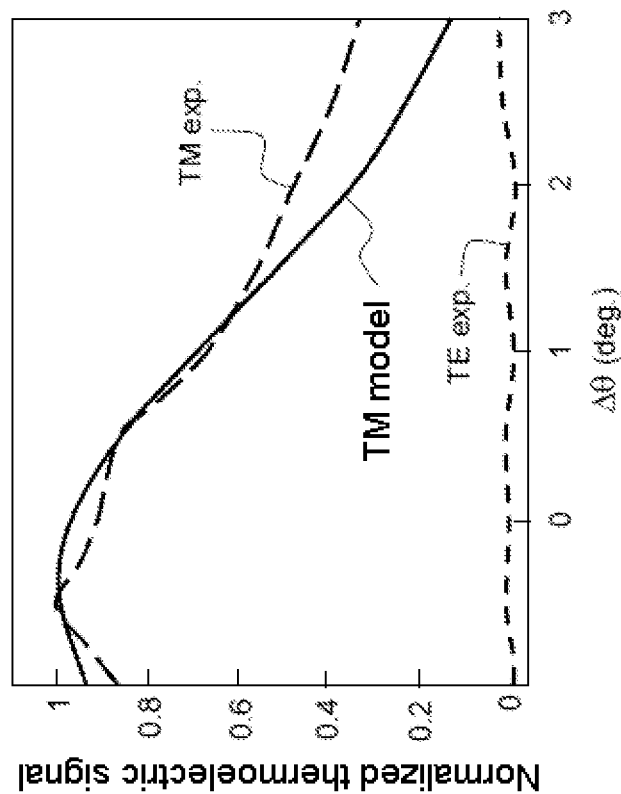
FIG. 4a illustrates the evolution of the voltage $V_{Ni-Ni}$ as a function of the incident polarization controlled by the angle $\alpha$ of the half-wave plate, and FIG. 4b that of the voltage $V_{Ni-Ni}$ as a function of the angle of incidence.
Figure 4A:
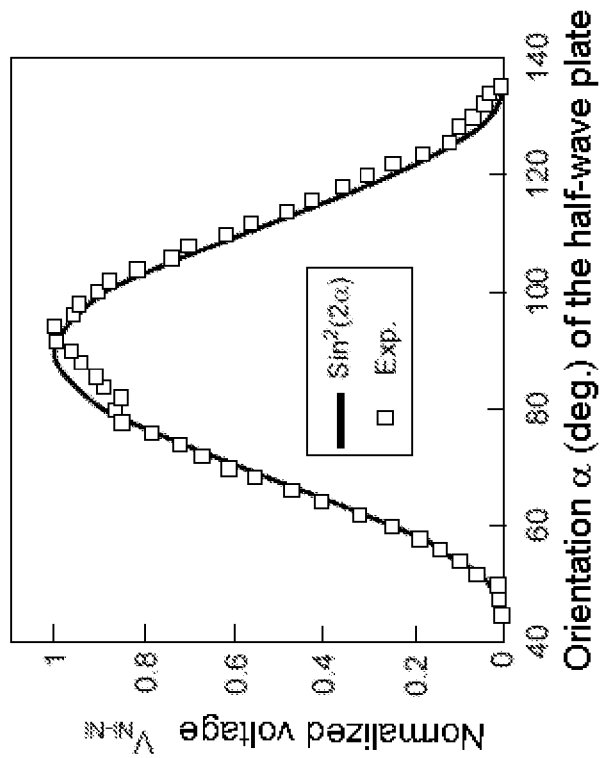

FIG. 4a shows the evolution of the voltage $V_{Ni-Ni}$ (measured after the spot centring procedure described hereinabove) as a function of the incident polarization controlled by the angle α of the half-wave plate. For α=45° and α=135°, the incident polarization is TE and the voltage $V_{Ni-Ni}$ is zero as expected on completion of the incident spot longitudinal centring procedure. On passing from the TE polarization to the TM polarization (corresponding to α=90°), it is noted that the voltage $V_{Ni-Ni}$ follows Malus' law thus proving that this voltage is proportional to the intensity of that component of the incident electric field making it possible to excite the plasmon mode. Thus, $V_{Ni-Ni}$ therefore does indeed appear to be characteristic of the power coupled in the plasmon mode.

With the aim of supplementing this first observation, FIG. 4b considers the evolution of the voltage $V_{Ni-Ni}$ as a function of the angle of incidence. In the case of the TE polarization, the voltage $V_{Ni-Ni}$ is zero for any angle. For the TM polarization, the voltage $V_{Ni-Ni}$ follows an evolution comparable to that of the numerically calculated power coupled in the plasmon mode. This second observation therefore confirms the conclusion according to which the voltage $V_{Ni-Ni}$ is proportional to the power coupled in the plasmon mode.

Figure 5:
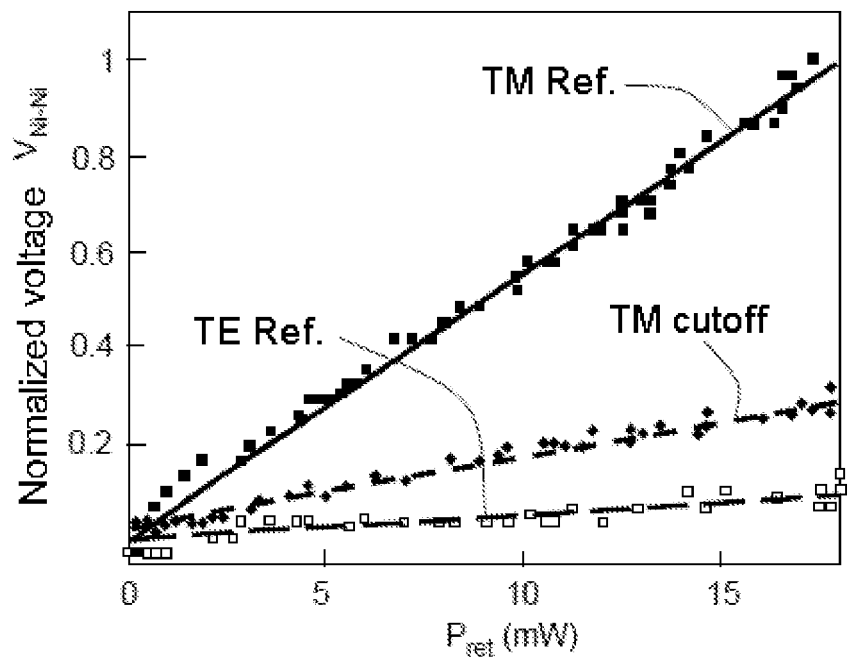
FIG. 5 illustrates the evolution of the voltage $V_{Ni-Ni}$ as a function of the reflected power $P_{ref}$.

With the aim of perfecting the demonstration, FIG. 5 considers the evolution of the voltage $V_{Ni-Ni}$ obtained after the procedure for centring the spot as a function of the reflected power (measured with the aid of a photodetector placed in the path of the ray reflected by the substrate of FIG. $2c_2$).

The reflected power $P_{ret}$ is proportional to the incident power. For an incident spot 11 whose characteristics (angle of incidence, spot size, angular divergence of the beam, etc.) are fixed, the power coupled in the plasmon mode is proportional to the incident power and therefore to the reflected power.

A plasmonic guide 2 exhibiting a constant width is considered first. For a TE incident polarization the voltage $V_{Ni-Ni}$ remains close to zero in spite of the fact that the absorption of the incident spot produces strong non-resonant heating of the system as attested to by a degradation (observed for reflected powers exceeding 25 mW) of the gold film at the level of the position of the incident spot. In the case of a TM incident polarization, the voltage $V_{Ni-Ni}$ grows in proportion to the reflected power and therefore to the power coupled in the plasmon mode. This proportionality ratio therefore does indeed make it possible to carry out a relative measurement of the power coupled in the plasmon mode.

A guide which exhibits a zone of the electrode 41a, 51a, whose width has been reduced to 500 nm under the cutoff width for the plasmon mode propagating along the gold strip, is now considered. Under these conditions, the plasmon mode excited on the launch zone may not couple to the strip plasmon mode and diffracts at the transition between the launch zone and the slender strip. For this configuration, and for a given reflected power, it is found that the voltage $V_{Ni-Ni}$ is of the order of 25% of the voltage measured in the case of the reference guide. In the absence of plasmon mode along the gold strip, a large decrease in the voltage $V_{Ni-Ni}$ is therefore observed. However, in the presence of the slender guide, this voltage is not zero. This is to do with the fact that the excitation of a plasmon mode on the launch zone contributes to the thermocouple voltage by way of the diffusion of heat along the slender gold strip. Thus, the coefficient of proportionality between the power coupled in the plasmon mode and the voltage $V_{Ni-Ni}$ is dependent on the opto-geometric characteristics of the electrode 41a, 51a of the thermocouple junctions which plays the role of plasmonic guide or in an equivalent manner of the characteristics of the plasmon mode (in particular its damping distance) propagating along this electrode.

A stationary state of the component obtained by the continuous excitation of the plasmon mode has been considered hitherto. This mode of excitation does not make it possible to characterize the response time of the thermoelectric detection. With the aim of alleviating this limitation, it is possible to integrate an electro-optical modulator into the experimental component of FIG. 2c. This device makes it possible to excite the plasmon mode with the aid of a laser pulse of a controlled duration.

Figure 6:
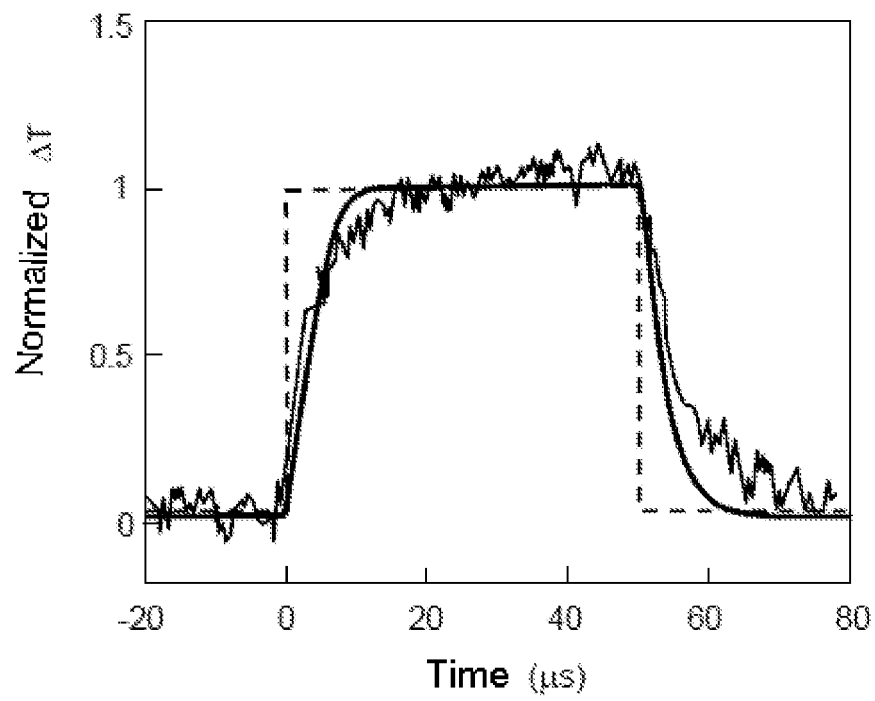
FIG. 6 shows three curves represented as a function of time, that of a pulse, that of the voltage $V_{Ni-Ni}$ and that of the temperature variation between the hot junction and the cold junction.

For a pulse with a duration of 50 μs shown in FIG. 6, a rise time of the thermoelectric signal of 10 μs and a fall time of 12 μs are observed, in good agreement with the simulation of the response time of the component. These response times indicate a cutoff frequency of the thermoelectric response of the order of 50 kHz, much greater than that of the thermo-resistive detection of the plasmon modes (600 Hz).

To summarize, we have shown that for a configuration corresponding to FIGS. $2c_1$ and $2c_2$, differential measurement of the voltage across the terminals of the hot and cold junctions makes it possible to obtain a signal proportional to the power coupled in the plasmon mode. This result is, however, obtained only on condition that the longitudinal position of the incident spot has been adjusted beforehand so as to eliminate the contribution to the voltage $V_{Ni-Ni}$ of the non-resonant heating of the system. This longitudinal centring of the spot constitutes an adaptation of the initialization procedure described previously in the particular case of the component of FIGS. $2c_1$ and $2c_2$.

The invention claimed is:

1. A thermoelectric component which comprises integrated into the component:
   a plasmonic waveguide,
   an exciter element for the guided plasmonic mode, and
   a device for measuring the power dissipated during propagation along the plasmonic waveguide,
   wherein the measurement device comprises, associated with the plasmonic guide, a thermocouple junction with two electrodes, one of the electrodes including the plasmonic waveguide.

2. The thermoelectric component according to claim 1, wherein the plasmonic guide is a ring resonator, and in that the exciter element is a plasmonic waveguide or a conventional waveguide.

3. The thermoelectric component according to claim 1, further comprising a second plasmonic guide and a second thermocouple junction with two electrodes, one of the electrodes of this second junction including the second plasmonic waveguide, the first plasmonic guide being disposed on one branch of a Y junction, the second plasmonic guide being disposed on the other branch of the Y junction.

4. The thermoelectric component according to claim 1, further comprising a second thermocouple junction with two electrodes, associated with the plasmonic guide, one of these electrodes being common to the first thermocouple junction and including the plasmonic waveguide, the first junction termed the hot junction being intended to be in the path of the plasmonic guided mode, the second junction termed the cold junction being situated away from the path of the plasmonic guided mode.

5. The thermoelectric component according to claim 4, wherein the exciter element for the guided mode comprises means for controlling its polarization.

6. The thermoelectric component according to claim 5, wherein the exciter element for the guided mode is a plasmonic or conventional input guide, coupled to the plasmonic guide by coupling of "butt-coupling" type or by directional coupling in the plane, or by vertical directional coupling, the exciter waveguide being buried in a substrate.

7. The thermoelectric component according to claim 5, wherein the exciter element for the guided mode is a micro diffraction grating whose lines are perpendicular to the longitudinal axis of the guide, intended to be coupled to a laser beam in unidirectional oblique incidence on the micro diffraction grating.

8. The thermoelectric component according to claim 7, wherein the micro diffraction grating is situated on the plasmonic guide at equal distance from the hot and cold thermocouple junctions, and the measurement device comprises only a single detection device for detecting small potential differences.

9. The thermoelectric component according to claim 5, wherein the exciter element for the guided mode is at an end of the plasmonic guide and is a micro diffraction grating whose lines are perpendicular to the longitudinal axis of the guide and which is intended to be coupled to a focused laser beam, at normal incidence on the micro diffraction grating, the part of the common electrode not including the plasmonic guide being disposed in a direction in which the micro grating has no coupling efficacy.

10. The thermoelectric component according to claim 5, wherein the exciter element for the guided mode is a laser beam focused at super-critical oblique incidence through a transparent substrate.

11. The thermoelectric component according to claim 4, wherein the power measurement device comprises a device for detecting potential differences by thermocouple junction and linked to these two devices, a circuit for processing the potential differences obtained.

12. A method of using a thermoelectric component according to claim 4, comprising a step of initializing the measurement device by non-resonant heating of the plasmonic guide.

13. The method of using a thermoelectric component according to claim 12, further comprising, subsequent to the initialization step, a step of exciting the guided mode in the plasmonic guide.

14. The method of using a thermoelectric component according to claim 12, further comprising, between the initialization step and the excitation step, a step of calibrating the measurement device.

15. The method of using a thermoelectric component according to claim 12, wherein the initialization step is carried out in a determined span of temperatures, and the step of exciting the guided mode is carried out for a temperature included in the said span of temperatures.

16. The thermoelectric component according to claim 1, further comprising an optical component excited by the plasmonic guide.

17. The thermoelectric component according to claim 1, wherein the electrode including the plasmonic guide is metallic.

18. The thermoelectric component according to claim 1, wherein the exciter element for the guided mode does not comprise any means for controlling its polarization.

19. The thermoelectric component according to claim 18, comprising a heating device situated at the input of the plasmonic guide.

20. The thermoelectric component according to claim 19, wherein the heating device comprises a Pelletier element, or a metallic strip of micronic width or a focused incident light beam.

21. The thermoelectric component according to claim 1, wherein the exciter element comprises modulation means.

* * * * *